US008039627B2

(12) United States Patent
Gano

(10) Patent No.: US 8,039,627 B2
(45) Date of Patent: Oct. 18, 2011

(54) SUBSTITUTED 3-ISOBUTYL-9,10-DIMETHOXY-1,3,4,6,7,11B-HEXAHYDRO-2H-PYRIDO[2,1-A]ISOQUINOLIN-2-OL COMPOUNDS AND METHODS RELATING THERETO

(75) Inventor: Kyle W. Gano, San Diego, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 698 days.

(21) Appl. No.: 11/937,445

(22) Filed: Nov. 8, 2007

(65) Prior Publication Data

US 2008/0167337 A1  Jul. 10, 2008

Related U.S. Application Data

(60) Provisional application No. 60/864,944, filed on Nov. 8, 2006.

(51) Int. Cl.
C07D 455/06 (2006.01)
A01N 43/42 (2006.01)
(52) U.S. Cl. ......................................... 546/95; 514/294
(58) Field of Classification Search ................... 546/95; 514/294
See application file for complete search history.

(56) References Cited

U.S. PATENT DOCUMENTS

| 2,843,591 A | 7/1958 | Brossi et al. |
| 2,852,518 A | 9/1958 | Morgan |
| 3,209,005 A | 9/1965 | Brossi et al. |
| 2003/0087803 A1 | 5/2003 | Latvin et al. |

FOREIGN PATENT DOCUMENTS

| WO | W091/16920 A1 | 11/1991 |
| WO | WO99/30561 A1 | 6/1999 |
| WO | WO2005/077946 A1 | 8/2005 |
| WO | WO2006/053067 A2 | 5/2006 |
| WO | WO2007/005283 A2 | 1/2007 |
| WO | WO2007/007105 A1 | 1/2007 |
| WO | W02007/017643 A1 | 2/2007 |
| WO | WO2007/017654 A1 | 2/2007 |

OTHER PUBLICATIONS

Aranda et al. European Journal of Medicinal Chemistry, 25, 369-374, 1990.*
Kilbourn et al. Chirality, 9, 59062, 1997.*
Vig et al. Pharmaceutical Research, 20 (9), 1381-1388, 2003.*
Cho et al., Annual Reports in Medicinal chemistry, 41, 395-407, 2006.*
Communication pursuant to Article 94(3) (Form 2906) in EP App. No. 07864160.2 mailed Aug. 13, 2009.
Stock, A. M. et al, Structure and Tautomerism of the Esters of Several beta-Substituted Pyruvic Acids, Journal of Organic Chemistry, 1958, 1840-1848, 23.
Brossi, A. et al, 2-Hydroxy-hydrobenzo[a]chinolizine, Helvetica Chimica Acta 1958, 1793-1806, 41.
Pletscher, A. et al, Benzoquinolizine Derivatives: A New Class of Monoamine Decreasing Drugs with Psychotropic Action, International Review of Neurobiology, 1962, 275-306.
Schwarz, D. E. et al, Metabolice Studies of Tetrabenazine, A Psychotropic Drug in Animals and Man, Biochemical Pharmacology, 1966, 645-655, 15.
Pritsch, L. E. et al, On the Pharmacology of a Benzoquinolizine Derivative: Ro-1284, Prarmacology 1969, 113-123, 2.
Mehvar, R. et al, Direct Injection High-Performance Liquid Chromatography of Tetrabenazine and Its Metabolite in Plasma of Humans and Rats, Journal of Pharmaceutical Sciences, 1986, 1006-1009, 75(10).
Mehvar, R. et al, Pharmacokinetics of Tetrabenazine and Is Major Metabolite in Man and Rat, Drug Metabolism and Disposition, 1987, 250-255, 15(2).
Aranda, G. et al, Synthesis and biological activity of iodinated and photosensitive derivatives of tetrabenazine, European Journal of Medicinal Chemistry, 1990, 369-374, 25.
Kilborn, M. et al, Binding of alpha-dihydrotetrabenazine to the vesicular monoamine transporter is stereospecific, European Journal of Pharmacology, 1995, 249-252, 278.
Lee, L. C., In Vitro and In Vivo Studies of Benzisoquinoline Ligands for the Brain Synaptic Vesicle Monoamine Transporter, Journal of Medicinal Chemistry, 1996, 191-196, 39.
Kilborn, M.R. et al, Absolute Configuration of (+)-alpha-Dihyrdotertabenazine, an Active Metabolite of Tetrabenazine. Chirality, 1997, 59-62, 9.
Vig, B. S. et al, Amino Acid Ester Prodrugs of Floxuridine: Synthesis and Effects of Structure, Stereochemistry, and Site of Esterification on the Rate of Hydrolysis, 2003, 1381-1388, 20(9). Kim, I. et al, A Novel Nucleoside Prodrug-Activating Enzyme: Substrate Specificity of Biphenyl Hydrolase-like Protein, Molecular Pharmaceutics, 2004, 117-127, 1(2).
Song, X., et al, Amino Acid Ester Prodrugs of the Anticancer Agent Gemcitabine: Synthesis, Bioconversion, Metabolic Bioevasion, and hPEPT1-Mediated Transport, Molecular Pharmaceutics, 2005, 157-167, 2(2).

(Continued)

*Primary Examiner* — Nizal Chandrakumar
(74) *Attorney, Agent, or Firm* — Seed IP Law Group PLLC

(57) ABSTRACT

Substituted 3-isobutyl-9,10-dimethoxy-1,3,4,6,7,11b-hexahydro-2H-pyrido[2,1-a]isoquinolin-2-ol compounds are disclosed that are inhibitors of the vesicular monoamine transporter 2 (VMAT2). The compounds of this invention have the structure:

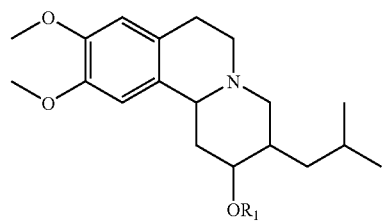

wherein $R_1$ is as defined herein, including stereoisomers and pharmaceutically acceptable salts and solvates thereof. Also disclosed are compositions containing a compound of this invention in combination with a pharmaceutically acceptable carrier, as well as methods relating to the use in a subject in need thereof.

2 Claims, 3 Drawing Sheets

OTHER PUBLICATIONS

Lorenz!, P. L. et al, Amino Acid Ester Prodrugs of 2-Bromo-5,6-dichloro-1-(beta-D-ribofuranosyl)benzimidazole Enhance Metabolic Stability in Vitro and in Vivo, The Journal of Pharmacology and Experimental Therapeutics, 2005, 883-890, 314(2).

Zheng, G. et al, Vesicular Monoamine Transporter 2: Role as a Novel Target for Drug Development, The AAPS Journal, 2006, 682-692, 8(4).

Cho, A., Recent Advances in Oral Prodrug Discovery, Annual Reports in Medicinal Chemistry, 2006, 395-407, 41.

Zheng, F. et al, Computational neural network analysis of the affinity of lobeline and tetrabenazine analogs for the vesicular monoamine transporter-2, Bioorganic and Medicinal Chemistry, 2007, 2975-2992, 15.

* cited by examiner

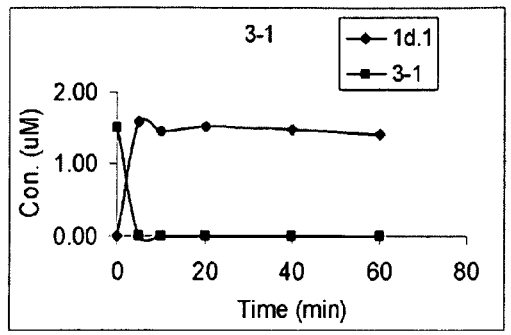
Figure 2a (rat)
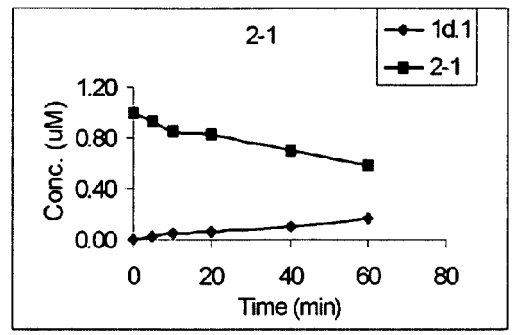
Figure 2b (rat)
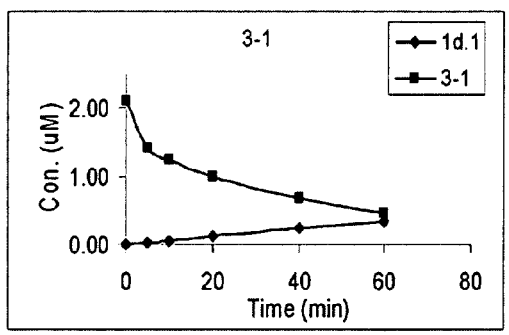
Figure 2c (dog)
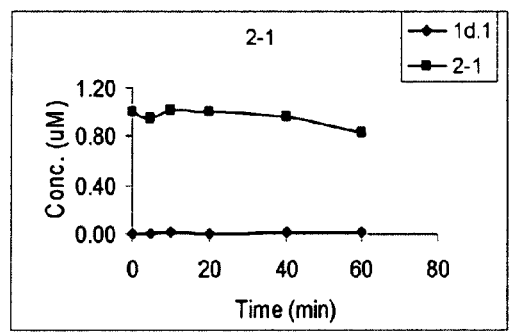
Figure 2d (dog)
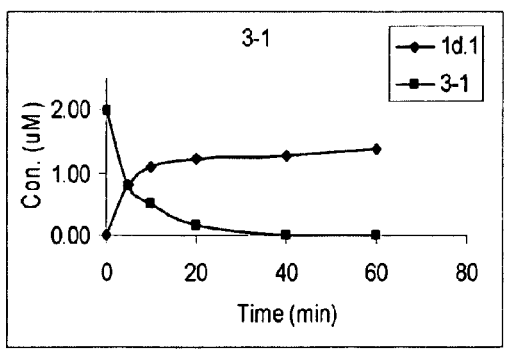
Figure 2e (human)
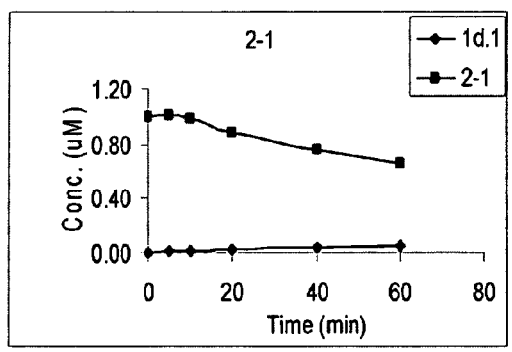
Figure 2f (human)

Plasma Concentration-Time Profile of
10 mg/kg PO of 3-1 and 10 mg/kg PO
of 1d.1 to male rats (N=3)

Plasma Concentration-Time Profile
of 10 mg/kg PO of 2-1 to Male Rats
(N=3)

Plasma Concentration-Time Profile
of 6.1 mg/kg PO of 3-1 to Male
Dogs (N=3)

Plasma Concentration-Time Profile
of 10 mg/kg PO of 2-1 to Male Dogs
(N=3)

SUBSTITUTED 3-ISOBUTYL-9,10-DIMETHOXY-1,3,4,6,7,11B-HEXAHYDRO-2H-PYRIDO[2,1-A]ISOQUINOLIN-2-OL COMPOUNDS AND METHODS RELATING THERETO

CROSS-REFERENCE TO RELATED APPLICATION

This application claims the benefit of U.S. Provisional Patent Application No. 60/864,944 filed Nov. 8, 2006, which application is incorporated herein by reference in its entirety.

FIELD OF THE INVENTION

This invention relates generally to substituted 3-isobutyl-9,10-dimethoxy-1,3,4,6,7,11b-hexahydro-2H-pyrido[2,1-a]isoquinolin-2-ol compounds, their preparation and to methods of treating disorders by administration of such compounds to a warm-blooded animal in need thereof.

BACKGROUND OF THE INVENTION

3-Isobutyl-9,10-dimethoxy-1,3,4,6,7,11b-hexahydro-2H-pyrido[2,1-a]isoquinolin-2-one, also known as tetrabenazine (TBZ), has been used as a drug for decades. Tetrabenazine is a potent, reversible inhibitor of catecholamine uptake by vesicular monoamine transporter-2 (VMAT2) (IC50=3.2 nM) (Scherman, et al, Proc. Natl. Acad. Sci. USA, (1983) 80:584-8) and is currently used in the treatment of various hyperkinetic movement disorders. Side effects associated with TBZ include sedation, depression, akathisia, and parkinsonism. Inhibition of VMAT2 by TBZ results in depletion of brain monoamines in vivo (Pettibone, D. J. et al., Eur. J. Pharmacol. (1984) 102:431-6). TBZ also inhibits presynaptic and postsynaptic dopamine receptors in rat brain (Login, I. S., et al., (1982) Ann. Neurology 12:257-62; Reches, et al, J. Pharmacol. Exp. Ther. (1983) 225:515-521). This off-target activity of TBZ may be responsible for some of the observed side effects.

TBZ, which contains two chiral centers and is a racemic mix of two stereoisomers, is rapidly and extensively metabolized in vivo to its reduced form, 3-isobutyl-9,10-dimethoxy-1,3,4,6,7,11b-hexahydro-2H-pyrido[2,1-a]isoquinolin-2-ol, also known as dihydrotetrabenazine (HTBZ). HTBZ is thought to exist as four individual isomers: (±) alpha-HTBZ and (±) beta-HTBZ. The 2R, 3R, 11bR or (+) alpha-HTBZ is believed to be the absolute configuration of the active metabolite (Chirality 1997 9:59-62). Despite its success in treating hyperkinetic disorders, tetrabenazine has a fairly low and variable bioavailability. Tetrabenazine administration to humans is complicated by extensive first pass metabolism and little or no tetrabenazine is observed in the urine.

There is a need in the art for analogs of tetrabenazine that provide the advantageous properties of tetrabenazine without exposing the body to all of stereoisomers of dihydrotetrabenazine. There is also a need for analogs of tetrabenazine that exhibit a longer half-life than tetrabenazine. There is likewise a need in the art for analogs of tetrabenazine that exhibit greater selectivity for VMAT2 than tetrabenazine. The present invention provides a tetrabenazine analog that exposes the body to a single stereoisomer of dihydrotetrabenazine, exhibits greater selectivity for VMAT2 than tetrabenazine, exhibits a longer half-life than tetrabenazine, and may exhibit lower variability in dose required from patient to patient.

BRIEF SUMMARY OF THE INVENTION

In brief, this invention is generally directed to substituted 3-isobutyl-9,10-dimethoxy-1,3,4,6,7,11b-hexahydro-2H-pyrido[2,1-a]isoquinolin-2-ol compounds, individual enantiomers thereof, as well as to methods for their preparation and use, and to pharmaceutical compositions containing the same. More specifically, the substituted 3-isobutyl-9,10-dimethoxy-1,3,4,6,7,11b-hexahydro-2H-pyrido[2,1-a]isoquinolin-2-ol compounds of this invention have the following general structure (I):

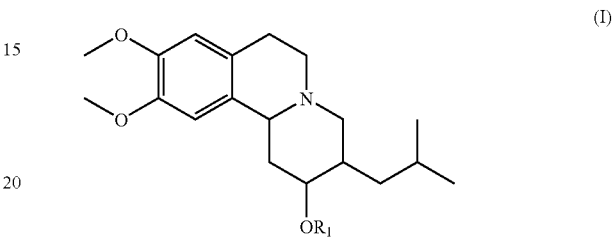

(I)

including stereoisomers and pharmaceutically acceptable salts and solvates thereof, wherein $R_1$ is as defined below.

The substituted 3-isobutyl-9,10-dimethoxy-1,3,4,6,7,11b-hexahydro-2H-pyrido[2,1-a]isoquinolin-2-ol compounds of this invention have utility over a wide range of therapeutic applications, and may be used to treat a variety of disorders including the family of hyperkinetic movement disorders. Additionally these compounds may prove useful in the treatment of other disease states or conditions which are associated with inhibition of the vesicular monoamine transporter 2 (VMAT2).

The methods of this invention include administering an effective amount of a substituted 3-isobutyl-9,10-dimethoxy-1,3,4,6,7,11b-hexahydro-2H-pyrido[2,1-a]isoquinolin-2-ol, preferably in the form of a pharmaceutical composition, to a mammal in need thereof. Thus, in still a further embodiment, pharmaceutical compositions are disclosed containing one or more substituted 3-isobutyl-9,10-dimethoxy-1,3,4,6,7,11b-hexahydro-2H-pyrido[2,1-a]isoquinolin-2-ol compounds of this invention in combination with a pharmaceutically acceptable carrier and/or diluent.

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE FIGURES

FIGS. 2a-2f comprise six graphs showing the stability profile of compounds 3-1 and 2-1 in rat, dog and human liver microsomes.

DETAILED DESCRIPTION OF THE INVENTION

Figure 1A:
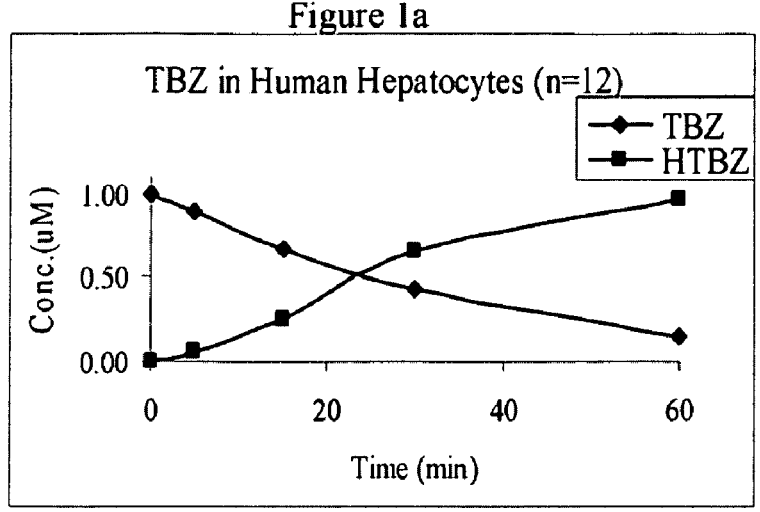
FIGS. 1a, 1b, and 1c comprise three graphs showing the conversion of tetrabenazine, compound 2-1 and compound 3-1 to their respective metabolites in human hepatocytes.

As mentioned above, the present invention is directed generally to substituted 3-isobutyl-9,10-dimethoxy-1,3,4,6,7, 11b-hexahydro-2H-pyrido[2,1-a]isoquinolin-2-ol compounds. The compounds of this invention have the following structure (I):

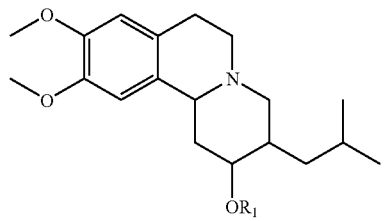
(I)

and stereoisomers, pharmaceutically acceptable salts and solvates thereof, wherein:

$R_1$ is a) —C(=O)—O-alkyl; or b) —C(=O)—$C_{1-6}$alkanediyl-$NH_2$, wherein said $C_{1-6}$alkanediyl is optionally substituted with a group selected from —NH—C(=NH)$NH_2$, —$CO_2H$, —$CO_2Me$, —SH, —C(O)$NH_2$, —$NH_2$, —$SCH_3$, phenyl, —OH, 4-hydroxy-phenyl, imidazolyl and indolyl.

As used herein, the above terms have the following meaning:

"Alkyl" means a straight chain or branched, noncyclic or cyclic, unsaturated or saturated aliphatic hydrocarbon containing from 1 to 10 carbon atoms, while the term "$C_{1-4}$alkyl" has the same meaning as alkyl but contains from 1 to 4 carbon atoms. "$C_{1-6}$alkyl" has the same meaning as alkyl but contains from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —$CH_2$-cyclopropyl, —$CH_2$-cyclobutyl, —$CH_2$-cyclopentyl, —$CH_2$-cyclohexyl, and the like; while unsaturated cyclic alkyls include cyclopentenyl and cyclohexenyl, and the like. Cyclic alkyls include di- and poly-homocyclic rings such as decalin and adamantyl. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.

"$C_{1-6}$alkanediyl" means a divalent $C_{1-6}$alkyl from which two hydrogen atoms are taken from the same carbon atom or from different carbon atoms, such as —$CH_2$—, —$CH_2CH_2$—, —CH($CH_3$)— —$CH_2CH_2CH_2$—, —CH($CH_3$)$CH_2CH_2$—, —$CH_2C(CH_3)_2CH_2$—, and the like.

"Amino acid residue" means an amino acid structure which lacks the hydroxyl of the α-carboxyl group. For example the alanine residue is —C(=O)—CH($NH_2$)$CH_3$.

In an embodiment, $R_1$ of structure (I) is —C(=O)O-alkyl as shown in structure (II) and in another embodiment, $R_1$ of structure (I) is —C(=O)—$C_{1-6}$alkanediyl -$NH_2$ as shown in structure (III).

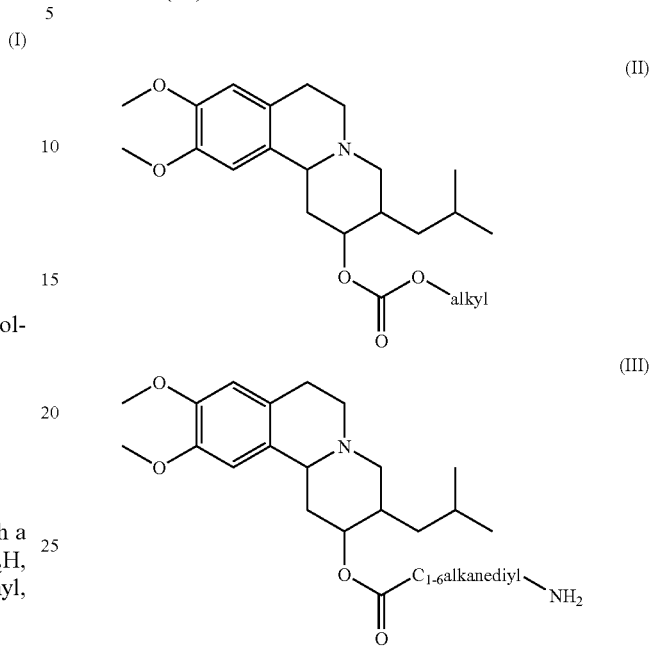

In an embodiment, the —$C_{1-6}$alkanediyl-$NH_2$ of structure (III) is (S)-1-amino-2-methyl-propan-1-yl as shown in structure (IV). Structure (V) shows an embodiment of structure (I) where $R_1$ is —C(=O)—$C_{1-6}$alkanediyl-$NH_2$ and the $C_{1-6}$alkanediyl is substituted with —COOH.

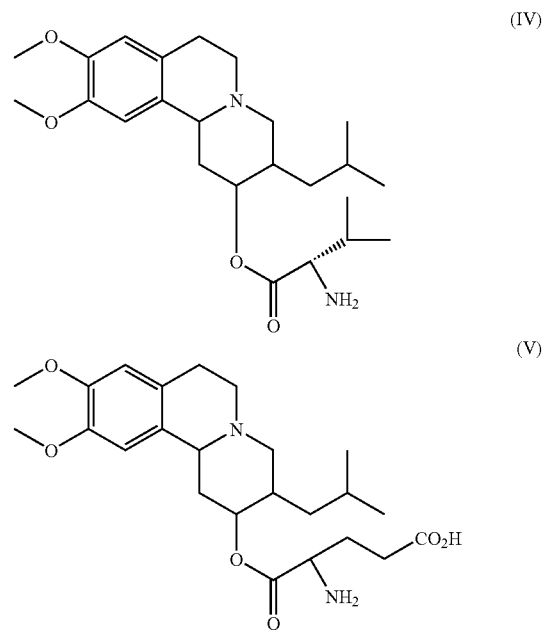

In additional embodiments, $R_1$ of structure (I) is an amino acid residue as shown in structure (VI). Structure (VII) shows an embodiment of structure (VI) where the amino acid residue is valine.

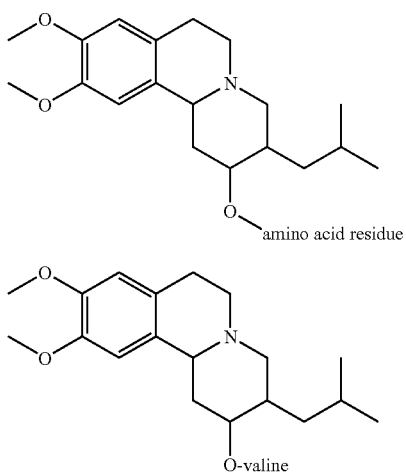

In an embodiment, compounds of the present invention may exist as the racemic mixture, as a diastereomeric pair or as the individual enantiomer or mix of enantiomers. Structure (VIII) shows the ring numbering for the substituted 3-isobutyl-9,10-dimethoxy-1,3,4,6,7,11b-hexahydro-2H-pyrido[2,1-a]isoquinolin-2-ol compounds of the invention. Stereocenters are located at the 2, 3, and 11b positions of the ring system. Compounds of the present invention include the 2R, 3R, 11bR configuration as well as the 2R, 3R, 11bS, the 2R, 3S, 11bR, the 2S, 3R, 11bR, the 2R, 3S, 11bS, the 2S, 3R, 11bS, the 2S, 3S, 11bR, and the 2S, 3S, 11bS. The 2R, 3R, 11bR and 2S, 3S, 11bS enantiomers are shown in structures (IX) and (X), respectively.

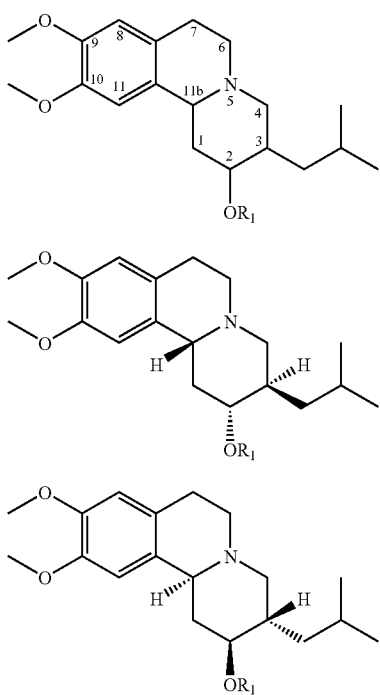

The compounds of the present invention may be prepared by known organic synthesis techniques, including the methods described in more detail in the Examples. In general, the compounds of structure (I) above may be made by the following reaction schemes, wherein all substituents are as defined above unless indicated otherwise.

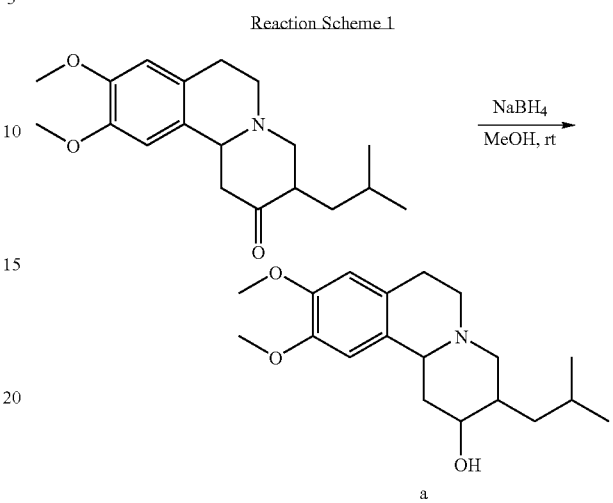

Reduction of a racemic mix of R,R and S,S tetrabenazine with a borohydride reducing agent gives dihydrotetrabenazine a. When the reducing agent is lithium tri-sec-butyl borohydride (L-Selectride), predominantly the 2S, 3R, 11bR and 2R, 3S, 11bS isomers are generated. Use of sodium borohydride results in a mix of all 4 stereoisomers. The remaining stereoisomers may be synthesized by taking any or all of the previously generated stereoisomers and reacting them with a dehydrating agent such as phosphorous pentachloride to form the unsaturated compound which is then stereoselectively rehydrated by, for instance, a hydroboration procedure using borane-THF to form a borane complex which is oxidized to the appropriate dihydrotetrabenazine with hydrogen peroxide (Clarke et al., WO2005077946). The racemic products can be further separated by chiral chromatography into the individual enantiomers by chiral chromatography.

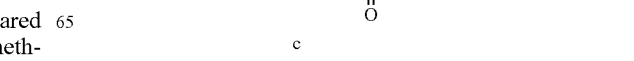

-continued

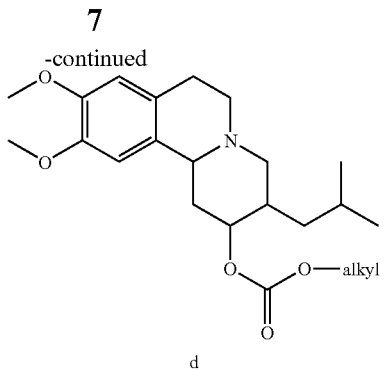

d

The chloroformate intermediate c may be generated by treating a with phosgene or triphosgene. Treatment of c with an alcohol in the presence of a base such as DMAP generates the carbonate product d. Alternatively, the carbonate d can be generated directly by treating the alcohol a with a pyrocarbonate under DMAP catalysis.

Reaction Scheme 3

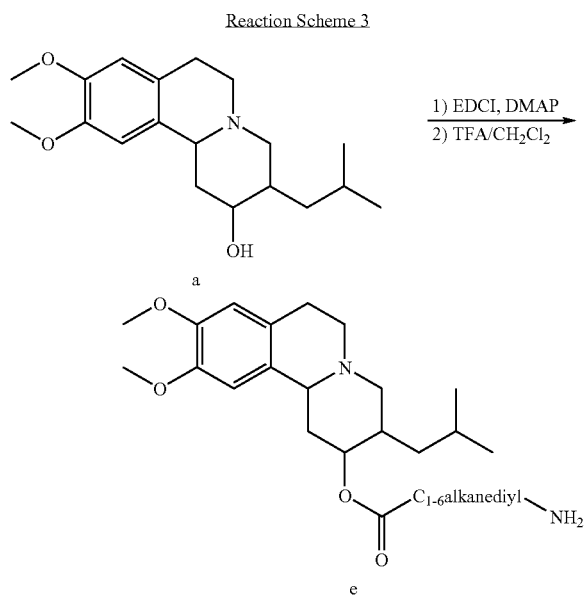

Dihydrotetrabenazine a is condensed with a BOC protected amino acid using 1-(3-dimethylaminopropyl)-3-ethylcarbodiimide hydrochloride (EDCI) and dimethylaminopyridine (DMAP) in dimethylformamide and methylene chloride, followed by deprotection of the BOC functionality with, for instance, a 50/50 trifluoroacetic acid/methylene chloride solution to give e. Alternatively, dihydrotetrabenazine a may be condensed with a CBZ-protected amino acid using DCC (1,3-dicyclohexylcarbodiimide) followed by deprotection of the CBZ functionality by hydrogenation under appropriate conditions.

Compounds of the present invention exhibit greater selectivity for VMAT2 than tetrabenazine. As a result, they may provide desirable properties of tetrabenazine without all of the undesirable side effects. In addition, as shown in FIGS. 3a-3d, certain compounds of this invention, such as, for example, compound 2-1, unexpectedly provide a longer duration of action than tetrabenazine. This may be particularly beneficial because it may allow an administration regimen that requires fewer doses per day than tetrabenazine. For example, while tetrabenazine is typically administered 2-3 times per day, certain compounds of this invention, such as, for example, compound 2-1, may be therapeutically effective when administered only once per day. Thus, because of the unexpectedly longer duration of action afforded by these compounds, once daily dosing may be attainable.

Compounds of the present invention include the following esters:

(S)-2-Amino-3-methyl-butyric acid 3-isobutyl-9,10-dimethoxy-1,3,4,6,7,11b-hexahydro-2H-pyrido[2,1-a]isoquinolin-2-yl ester Compounds of the present invention include the following carbonates:

Carbonic acid ethyl ester 3-isobutyl-9,10-dimethoxy-1,3,4,6,7,11b-hexahydro-2H-pyrido[2,1-a]isoquinolin-2-yl ester;

Carbonic acid butyl ester 3-isobutyl-9,10-dimethoxy-1,3,4,6,7,11b-hexahydro-2H-pyrido[2,1-a]isoquinolin-2-yl ester;

Carbonic acid pentyl ester 3-isobutyl-9,10-dimethoxy-1,3,4,6,7,11b-hexahydro-2H-pyrido[2,1-a]isoquinolin-2-yl ester;

Carbonic acid isobutyl ester 3-isobutyl-9,10-dimethoxy-1,3,4,6,7,11b-hexahydro-2H-pyrido[2,1-a]isoquinolin-2-yl ester;

Carbonic acid sec-butyl ester 3-isobutyl-9,10-dimethoxy-1,3,4,6,7,11b-hexahydro-2H-pyrido[2,1-a]isoquinolin-2-yl ester;

Carbonic acid 3-methyl-butyl ester 3-isobutyl-9,10-dimethoxy-1,3,4,6,7,11b-hexahydro-2H-pyrido[2,1-a]isoquinolin-2-yl ester; and Carbonic acid tert-butyl ester 3-isobutyl-9,10-dimethoxy-1,3,4,6,7,11b-hexahydro-2H-pyrido[2,1-a]isoquinolin-2-yl ester.

The compounds of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of structure (I) is intended to encompass any and all acceptable salt forms.

With regard to stereoisomers, the compounds of structure (I) may have chiral centers and may occur as racemates, racemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

As mentioned above, the compounds of this invention and their salts may reduce the supply of monoamines in the central nervous system by inhibiting the human monoamine transporter isoform 2 (VMAT2). As such, these compounds and their salts may have utility over a wide range of therapeutic applications, and may be used to treat a variety of disorders which are caused by or linked to inhibition of the human monoamine transporter isoform 2. These disorders include hyperkinetic disorders.

In an embodiment, conditions which may be treated by compounds of the current invention include, but are not limited to, treatment of hyperkinetic disorders such as Huntington's disease, tardive dyskinesia, Tourette's syndrome, and tics.

In another embodiment of the invention, the compounds of this invention and their salts may be hydrolyzed in the body of a mammal to compounds that may inhibit the human monoamine transporter isoform 2. As such, these compounds and their salts may have additional utility in altering the in vivo properties of the metabolite in a mammal such as the maximum concentration or duration of action.

In another embodiment of the invention, pharmaceutical compositions containing one or more monoamine re-uptake inhibitors are disclosed. For the purposes of administration, the compounds of the present invention may be formulated as pharmaceutical compositions. Pharmaceutical compositions of the present invention comprise a monoamine re-uptake inhibitor of the present invention and a pharmaceutically acceptable carrier and/or diluent. The VMAT2 inhibitor is present in the composition in an amount which is effective to treat a particular disorder—that is, in an amount sufficient to reduce the supply of monoamines in the central nervous system, and preferably with acceptable toxicity to the patient. Appropriate concentrations and dosages can be readily determined by one skilled in the art.

Pharmaceutically acceptable carriers and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a VMAT2 inhibitor, diluents, dispersing and surface active agents, binders, and lubricants. One skilled in this art may further formulate the VMAT2 inhibitor in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for treating disorders of the central or peripheral nervous system. Such methods include administering a compound of the present invention to a warm-blooded animal in an amount sufficient to treat the condition. In this context, "treat" includes prophylactic administration. Such methods include systemic administration of a VMAT2 inhibitor of this invention, preferably in the form of a pharmaceutical composition as discussed above. As used herein, systemic administration includes oral and parenteral methods of administration. For oral administration, suitable pharmaceutical compositions include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the VMAT2 inhibitor, buffers, antioxidants, bacteriostats, and other additives commonly employed in such solutions.

EXAMPLES

HPLC Methods for Analyzing the Samples
Retention time, $t_R$, in minutes
Analytical HPLC-MS Method 1
Platform: Agilent 1100 series: equipped with an auto-sampler, an UV detector (220 nM and 254 nM), a MS detector (APCI);
HPLC column: Phenomenex Synergi-Max RP 80A, 2.0×50 mm column;
HPLC gradient: 1.0 mL/minute, from 10% acetonitrile in water to 90% acetonitrile in water in 2.5 minutes, maintaining 90% for 1 minute. Both acetonitrile and water have 0.025% TFA.
Analytical HPLC-MS Method 2
Platform: Agilent 1100 series: equipped with an auto-sampler, an UV detector (220 nM and 254 nM), a MS detector (APCI);
HPLC column: Phenomenex Synergi-Max RP 80A, 2.0×50 mm column;
HPLC gradient: 1.0 mL/minute, from 5% acetonitrile in water to 95% acetonitrile in water in 13.5 minutes, maintaining 95% for 2 minute. Both acetonitrile and water have 0.025% TFA.
Analytical HPLC-MS Method 3
Platform: Gilson 215 Auto-sampler, Dionex Thermostatted Column Compartment TCC-100 held at 30° C., Dionex PDA-100 Photodiode Array Detector (220 nm and 254 nm), Dionex P680 HPLC pump, Thermo Finnigan MSQ single quad Mass Spectrometer (APCI)
HPLC column: Phenomenex Gemini 5μ C18 110A, 4.6×150 mm
HPLC gradient: 2.5 mL/min, from 5% acetonitrile in water to 90% acetonitrile in water in 9.86 minutes, from 90% acetonitrile in water to 95% acetonitrile in water in 0.1 minutes, hold at 95% for 1.19 minutes. Both acetonitrile and water have 0.04% $NH_4OH$.
Analytical HPLC-MS Method 4
Platform: Gilson 215 Auto-sampler, Dionex Thermostatted Column Compartment TCC-100 held at 30° C., Dionex PDA-100 Photodiode Array Detector (220 nm and 254 nm), Dionex P680 HPLC pump, Thermo Finnigan MSQ single quad Mass Spectrometer (APCI)
HPLC column: Phenomenex Gemini 5μ C18 110A, 3.0×150 mm
HPLC gradient: 1.5 mL/min, from 5% acetonitrile in water to 90% acetonitrile in water in 9.86 minutes, from 90% acetonitrile in water to 95% acetonitrile in water in 0.1 minutes, hold at 95% for 1.19 minutes. Both acetonitrile and water have 0.04% $NH_4OH$
Chiral Supercritical Fluid Chromatography for Chiral Separation Method 1
Platform: Berger Multigram II SFC system from Autochem
Column: Chiralcel OD-H, 2.1×25 cm, SFC column
Modifier: 20% methanol
Flow rate: 60 mL/min
Pressure: 100 bar
Oven temperature: 35° C.
Loading: approximately 14 mg/injection (methanol)
Chiral Supercritical Fluid Chromatography for Chiral Separation Method 2

Platform: Berger Multigram II SFC system from Autochem
Column: chiralpak AS-H, 2.1×25 cm, SFC column
Modifier: 20% methanol
Flow rate: 60 mL/min
Pressure: 100 bar
Oven Temperature: 35° C.
Loading: 40 mg/injection (MeOH)

Chiral Supercritical Fluid Chromatography for Chiral Separation Method 3
Column: Chiralpak IA, 2.1×25 cm, SFC column
Modifier: 28% (Methanol/Acetone=7:3)
Flow rate: 55 mL/min
Pressure: 100 bar
Oven Temperature: 35° C.
Loading: 50 mg/injection The sample was dissolved in 1:1 mixture of Methanol/Acetone. The final concentration was 50 mg/mL.

EXAMPLE 1

(2R,3R,11bR)-3-isobutyl-9,10-dimethoxy-1,3,4,6,7,11b-hexahydro-2H-pyrido[2,1-a]isoquinolin-2-ol ((2R,3R,11bR)-dihydrotetrabenazine)

Step 1A: 3-Dimethylaminomethyl-5-methyl-hexan-2-one

Dimethylamine HCl (90 g, 1.1 mol), 5-methyl-2-hexanone (450 mL, 3.3 mol), and paraformaldehyde (50 g, 1.7 mol) were suspended in MeOH (80 mL) and concentrated HCl (200 µL) was added. The reaction mixture was heated to 80° C. for 12 hours. The mixture was allowed to cool to room temperature and 10% NaOH was added until basic. The entire mixture was extracted with $Et_2O$ (100 mL, 2×). The organic layer was dried over $MgSO_4$ and concentrated. The crude reaction mixture was columned via flash column chromatography (0.5:9.5 MeOH:$CH_2Cl_2$) to give 30 g (175 mmol) of 3-dimethylaminomethyl-5-methyl-hexan-2-one 1a in a 16% yield.

Step 1B: 3-Dimethylaminomethyl-5-methyl-hexan-2-One methiodide

To a round bottom flask was added 3-dimethylaminomethyl-5-methyl-hexan-2-one 1a (30 g, 175 mmol) and EtOAc (300 mL) followed by methyl iodide (22 mL, 351 mmol). The mixture was stirred overnight and a white precipitate formed. The precipitate was filtered, washed with $Et_2O$ (150 mL, 3×) and dried to yield 3-dimethylaminomethyl-5-methyl-hexan-2-one methiodide 1b (44.9 g, 81% yield) as a fluffy white solid.

Step 1C: Tetrabenazine

To a round bottom flask was added 6,7-dimethoxy-3,4-dihydroisoquinoline (13 g, 67.8 mmol), 3-dimethylaminomethyl-5-methyl-hexan-2-one methiodide 1b (26 g, 81.4 mmol) and EtOH (130 mL). The suspension was heated to 80° C. overnight. The reaction mixture was allowed to cool to room temperature and $H_2O$ (200 mL) was added forming a precipitate. The EtOH was removed in vacuo and $CH_2Cl_2$ (400 mL) was added. A 10% NaOH solution was added to the mixture until basic. The aqueous layer was then extracted 3× with $CH_2Cl_2$ (250 mL). The organic layers were combined, dried over $MgSO_4$ and concentrated. The crude reaction mixture was purified via flash column chromatography (0.5:9.5 Acetone:$CH_2Cl_2$) and further recrystallized from EtOAc and Hexanes to give 16.1 g (51 mmol) of a racemic mix of (3S, 11bS) and (3R,11bR)-3-isobutyl-9,10-dimethoxy-1,3,4,6,7,11b-hexahydro-pyrido[2,1-a]isoquinolin-2-one 1c (tetrabenazine, TBZ) in a 75% yield. The enantiomers of tetrabenazine were separated by SFC utilizing a Chiralpak AD-H column with 15% CAN/MeOH plus 0.5% DMEA at 2.5 mL/min at 100 bar and 35° C. to yield 4.3 g of (3R,11bR)-tetrabenazine 1c.1 and 4.3 g of (3S,11bS)-tetrabenazine 1c.2. (3R,11bR)-tetrabenazine 1c.1: MS calcd: (317); Found 318.7 (M+H). (3S,11bS)-tetrabenazine 1c.2: MS calcd: (317); Found 318.7 (M+H).

Step 1D: (2R,3R,11bR)-3-Isobutyl-9,10-dimethoxy-1,3,4,6,7,11b-hexahydro-2H-pyrido[2,1-a]isoquinolin-2-ol (3R,11bR)-Tetrabenazine 1c.1 (2 g, 6.3 mmol) was dissolved in EtOH (70 mL) and cooled to 0° C. Sodium borohydride (261 mg, 6.9 mmol) was then added in portions at 0° C. The reaction was complete after 30 minutes and quenched with saturated $NH_4Cl$ (4 mL). The white precipitate formed was filtered and washed with EtOH (5 mL, 2×). The EtOH was removed in vacuo and the aqueous layer extracted 3× with $CH_2Cl_2$ (50 mL). The organic layers were combined, dried over $MgSO_4$ and concentrated. The crude product was purified via flash column chromatography (0.5:9.5 MeOH:$CH_2Cl_2$) to give 1.6 g (5 mmol) of (2R,3R,11bR)-3-isobutyl-9,10-dimethoxy-1,3,4,6,7,11b-hexahydro-2H-pyrido[2,1-a]isoquinolin-2-ol ((2R,3R,11bR)-dihydrotetrabenazine) 1d.1 and 410 mg (1.3 mmol) of (2S,3R,11bR)-3-isobutyl-9,10-dimethoxy-1,3,4,6,7,11b-hexahydro-2H-pyrido[2,1-a]isoquinolin-2-ol ((2S,3R,1bR)-dihydrotetrabenazine) 1d.2. (2R,3R,11bR)-Dihydrotetrabenazine 1d.1: MS calcd: (319); Found 320.3 (M+H). (2S,3R,11bR)-Dihydrotetrabenazine 1d.2: MS calcd: (319); Found 320.3 (M+H).

EXAMPLE 2

(S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester Step 2A: (S)-2-Amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester 2-1

(2R,3R,11bR)-3-Isobutyl-9,10-dimethoxy-1,3,4,6,7,11b-hexahydro-2H-pyrido[2,1-a]isoquinolin-2-ol 1d.1 (200 mg, 0.63 mmol) was dissolved in 3 mL anhydrous $CH_2Cl_2$ and DMAP (75.0 mg, 0.63 mmol) and Cbz-L-valine (190 mg, 0.75 mmol) were added and the mixture stirred for 5 min. DCC (155 mg, 0.75 mmol) was added and a white precipitate formed immediately. The mixture was stirred overnight then filtered and concentrated. Purification via flash column chromatography (0.2:9.8, MeOH:$CH_2Cl_2$) gave 360 mg (0.63 mmol) of 2-benzyloxycarbonylamino-3-methyl-butyric acid (2R,3R,1bR)-3-isobutyl-9,10-dimethoxy-1,3,4,6,7,11b-hexahydro-2H-pyrido[2,1-a]isoquinolin-2-yl ester 2a as a pale yellow solid in quantitative yield. Compound 2a (163 mg, 0.29 mmol) was dissolved in MeOH (10 mL) and Pd/C was added and the mixture was purged with $H_2$. The mixture was stirred overnight, filtered through celite and concentrated. Purification via flash column chromatography (0.5:9.5, MeOH:$CH_2Cl_2$) gave 105 mg (0.25 mmol) of (S)-2-amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester 2-1 in 85% yield. MS calcd: (419); Found 419.3 (M+H)

Additional compounds synthesized by the same procedure using different amino acids include:

(R)-2-Amino-4-methyl-pentanoic acid (2R,3R,1bR)-3-isobutyl-9,10-dimethoxy-1,3,4,6,7,11b-hexahydro-2H-pyrido[2,1-a]isoquinolin-2-yl ester 2-2. MS calcd: (433); Found 433.4 (M+H)

(S)-2-Amino-4-methyl-pentanoic acid (2R,3R,11bR)-3-isobutyl-9,10-dimethoxy-1,3,4,6,7,11b-hexahydro-2H-pyrido[2,1-a]isoquinolin-2-yl ester 2-3. MS calcd: (433); Found 433.4 (M+H)

(S)-2-Amino-succinic acid 1-((2R,3R,11bR)-3-isobutyl-9,10-dimethoxy-1,3,4,6,7,11b-hexahydro-2H-pyrido[2,1-a]isoquinolin-2-yl) ester 4-methyl ester 2-4. MS calcd: (449); Found 449.3 (M+H)

2-Amino-2-methyl-propionic acid (2R,3R,11bR)-3-isobutyl-9,10-dimethoxy-1,3,4,6,7,11b-hexahydro-2H-pyrido[2,1-a]isoquinolin-2-yl ester 2-5. MS calcd: (405); Found 405.3 (M+H)

(R)-2-Amino-propionic acid (2R,3R,11bR)-3-isobutyl-9,10-dimethoxy-1,3,4,6,7,11b-hexahydro-2H-pyrido[2,1-a]isoquinolin-2-yl ester 2-6. MS calcd: (391); Found 391.3 (M+H)

(S)-2-Amino-propionic acid (2R,3R,11bR)-3-isobutyl-9,10-dimethoxy-1,3,4,6,7,11b-hexahydro-2H-pyrido[2,1-a]isoquinolin-2-yl ester 2-7. MS calcd: (391); Found 391.3 (M+H)

(R)-2-Amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester 2-8. MS calcd: (419); Found 419.4 (M+H)

Amino-acetic acid (2R,3R,11bR)-3-isobutyl-9,10-dimethoxy-1,3,4,6,7,11b-hexahydro-2H-pyrido[2,1-a]isoquinolin-2-yl ester 2-9. MS calcd: (377); Found 377.3 (M+H)

EXAMPLE 3

Carbonic acid ethyl ester (2R,3R,11bR)-3-isobutyl-9,10-dimethoxy-1,3,4,6,7,11b-hexahydro-2H-pyrido[2,1-a]isoquinolin-2-yl ester Step 3A: Carbonic acid ethyl ester (2R,3R,11bR)-3-isobutyl-9,10-dimethoxy-1,3,4,6,7,11b-hexahydro-2H-pyrido[2,1-a]isoquinolin-2-yl ester 3-1

(2R,3R,11bR)-3-Isobutyl-9,10-dimethoxy-1,3,4,6,7,11b-hexahydro-2H-pyrido[2,1-a]isoquinolin-2-ol 1d.1 (100 mg, 0.31 mmol) was dissolved in 3 mL anhydrous $CH_2Cl_2$ and DMAP (1.0 mg, 0.01 mmol) and pyridine (51 µL, 0.63 mmol) were added followed by dropwise addition of ethyl chloroformate (45 µL, 0.47 mmol). The reaction was allowed to stir overnight and diluted with $CH_2Cl_2$ (10 mL) and extracted from sat $NH_4Cl$ (5 mL). The organic layer was dried over $MgSO_4$ and concentrated. The crude product was purified via flash column chromatography (1:9, acetone:$CH_2Cl_2$) to give 88 mg (2.25 mmol) of 3-1 as a pale yellow foam in 72% yield. MS calcd: (392); Found 392.3 (M+H).

Also prepared by the above procedure were:

Carbonic acid methyl ester (2R,3R,11bR)-3-isobutyl-9,10-dimethoxy-1,3,4,6,7,11b-hexahydro-2H-pyrido[2,1-a]isoquinolin-2-yl ester 3-2 in 37% yield. MS calcd: (378); Found 378.1 (M+H)

Carbonic acid butyl ester (2R,3R,11bR)-3-isobutyl-9,10-dimethoxy-1,3,4,6,7,11b-hexahydro-2H-pyrido[2,1-a]isoquinolin-2-yl ester 3-3 in 46% yield. MS calcd: (420); Found 420.1 (M+H)

EXAMPLE 4

Method to Determine Stability of Compounds in Human Hepatocytes

Cryopreserved human hepatocytes from 12 individual donors were thawed according to the supplier's instruction and pooled. Cell viability was determined to be more than 85%. TBZ (1 µM) was incubated with individual human hepatocytes (1×10$^6$ cells/mL) at 37° C. with 95% $O_2$ and 5% $CO_2$ for 0, 5, 15, 30 and 60 min. TBZ in DMSO was added to achieve 1.0 µM (DMSO was less than 0.5% v/v). All concentrations and cell contents were relative to the final incubation volume of 100 µL. The incubation was terminated by mixing 100 µL of ice-cold acetonitrile in 1% formic acid containing dextromethorphan (1.0 µM) as internal standard for LC/MS analysis. Precipitated proteins were removed by centrifugation (1500-2500×g for 30 min at 15° C.).

Briefly, samples were separated with a gradient HPLC method by Acquity UPLC systems consisting of a pump, a column heater (40° C.), and a vacuum degasser/mobile phase tray. Mobile phase A was water in 0.1% formic acid and mobile phase B was acetonitrile in 0.1% formic acid. The gradient elution was as follows: mobile phase B: 0-10% at 0-0.75 min, 40-90% at 1.25-1.5 min, 90-0% at 1.75-2.0 min, and run time was 3 min. The reverse phase column was a BEH C18 column (50×2.1 mm, 1.7 µm). Flow rate was 0.8 mL/min and injection volume was 7.5 µL. The samples were monitored with API-3000 mass spectrometer and ESI ion source in positive mode, TBZ m/z 318.4 >220.4, HTBZ m/z 320.3>302.3, and dextromethorphan m/z 272.2>147.2.

Figure 1B:
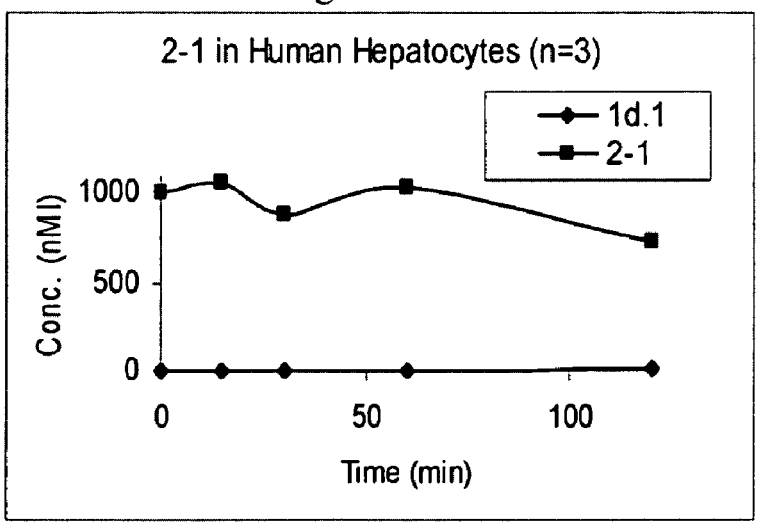
Figure 1C:
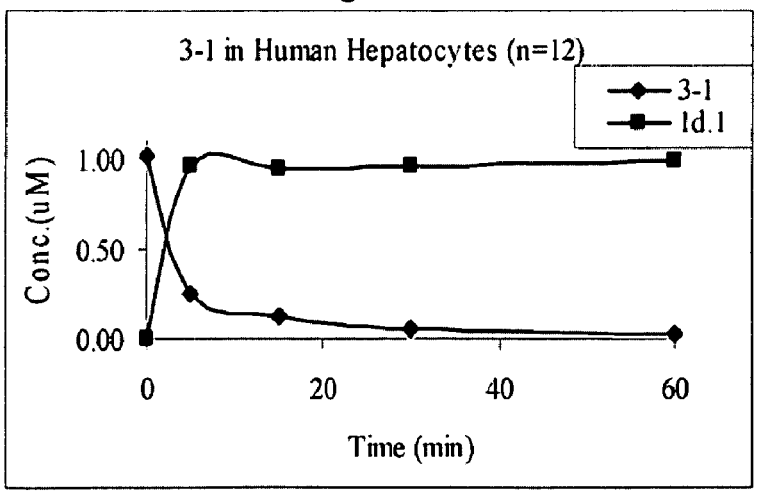

FIGS. 1a, 1b, and 1c show the conversion of tetrabenazine, compound 2-1 and compound 3-1 in human hepatocytes to HTBZ in the case of tetrabenazine and to 1d.1 in the case of compounds 2-1 and 3-1. Tetrabenazine and compound 3-1 showed this conversion to be rapid while compound 2-1 was comparatively slow.

EXAMPLE 5

Method to Determine Stability of Compounds in Mammalian Liver Microsomes

Briefly, pooled human liver microsomes (0.1 or 0.5 mg/mL; n>10; mixed gender) were incubated at 37° C. with the test compound in the presence of an NADPH-generating system containing 50 mM, pH 7.4 potassium phosphate buffer, 3 mM magnesium chloride, 1 mM EDTA, 1 mM NADP, 5 mM G-6-P, and 1 Unit/mL G-6-PD.

Incubations were conducted in six modified 2.0-mL, 96-well, deep-well plates in 1 µM of each compound (0.01% DMSO) with a total volume of 250 µl. Each plate, representing a single time point, contained 96 Titertube® Micro Tubes allowing for duplicates of 48 compounds at each time point (0, 5, 10, 20, 40, and 60 minutes). Reaction was stopped by the addition of an appropriate stop reagent (0.3 mL of acetonitrile containing a proprietary internal standard). Precipitated proteins were removed by centrifugation for 15 min at 3000 rpm, and the supernatant fluid (~0.1 mL) was analyzed by LC/MS for the % of parent compound remaining.

Samples were separated with a gradient HPLC method by Agilent LC systems consisting of a pump, a column heater (40° C.), and a vacuum degasser/mobile phase tray. Mobile phase A was water in 0.1% formic acid and mobile phase B was acetonitrile in 0.1% formic acid. The gradient elution was as follows: mobile phase B: 0-30% at 0-0.30 min, 30-98% at 0.7-1.1 min, 98-0% at 1.50-1.51 min, and run time was 3 min for 3-1; mobile phase B: 5-98% at 0.5-2.5 min, 98-5% at 4.0-4.1 min, and run time was 6.5 min for 2-1. The reverse phase column was a Luna C18 column (20×2 mm, 5 µm) for 3-1 and Synergi C18 column (150×2 mm, 5 µm) for 2-1. Flow rate was 0.55 mL/min for 3-1 and 0.4 mL/min for 2-1 and injection volume was 20 µL. The samples were monitored with API-3000 mass spectrometer and ESI ion source in positive mode, TBZ m/z 318.4>220.4, HTBZ m/z 320.3>302.3, and dextromethorphan m/z 272.2>147.2.

FIGS. 2a through 2f show the conversion of compound 2-1 and compound 3-1 in rat, dog, and human liver microsomes to 1d.1. In each of the species, conversion of compound 2-1 to 1d.1 was slower than the conversion seen in the case of compound 3-1 to compound 1d.1.

EXAMPLE 6

Pharmacokinetic (PK) Evaluation

Animal Method:
1. Rat

In brief, single oral dose (10 mg/kg) of 2-1 and 3-1 in 10% PEG in 0.25% methylcellulose in milli Q water was administered to rats (3 rats/dose) for a pharmacokinetic evaluation. Serial sampling was used to collect blood samples, which were taken from each treated animal at nine time points ranging from pre-dose to 24 hours post dose (0, 0.25, 0.5, 1, 2, 4, 6, 8 and 24 hours) for the oral administration. Plasma samples were stored at −80° C. or below until analysis.

2. Dog

In brief, a single oral dose (6.1 mg/kg for 3-1 and 10 mg/kg for 2-1) in 10% PEG in 0.25% methylcellulose in milli Q water was administered to dogs (3 dogs/dose) for a pharmacokinetic evaluation. Serial sampling was used to collect blood samples, which were taken from each treated animal at nine time points ranging from pre-dose to 24 hours post dose (0, 0.25, 0.5, 1, 1.5, 2, 4, 6, 8, 12, 24, 36 and 48 hours) for the oral administration. Plasma samples were stored at −80° C. or below until analysis.

General Bioanalytical Method:

Plasma samples were thawed on ice, and 50 µL of plasma was transferred to a 96-well plate. Plasma proteins were precipitated by addition of pre-chilled 150 µL acetonitrile (ACN) containing 75 ng/mL internal standard. Additional 50 µL of ACN/water (60:40) was added into each sample. Calibration curve samples were prepared by a serial dilution in ACN/water (60:40). Fifty microliter of each standard sample was transferred to a 96-well plate followed by adding 150 µL acetonitrile (ACN) containing 75 ng/mL internal standard and 50 µL blank rat plasma. The plates were capped, mixed and centrifuged at 3000 rpm for 20 min. The supernatant was collected and injected into a LC-MS/MS system for quantification. The non-validated assay method showed good linearity, specificity and accuracy for 3-1, 2-1 and 1d.1 over the concentration range of 1 to 1000 ng/mL and the low limit of quantification of 3-1, 2-1 and 1d.1 were all at 1 ng/mL. Three sets of QC samples (4, 40, 400, 800 ng/ml) for 3-1, 2-1 and 1d.1 were used as quality control for the studies needed and prepared in a same way as the standards. Quantification was performed by fitting peak area ratios to a weighted ($1/x^2$) linear calibration curve.

Pharmacokinetic Method:

Descriptive pharmacokinetics were derived and evaluated based on the plasma concentrations of 3-1, 2-1 and 1d.1 from each individual rat. Pharmacokinetic parameters were determined using Non-Compartmental Analysis of the plasma concentration-time profiles of 3-1, 2-1 and 1d.1 in WinNonlin pharmacokinetic modeling software Professional Version 5.0.1 program (Pharsight Corporation, Mountain View, Calif.).

Figure 3A:
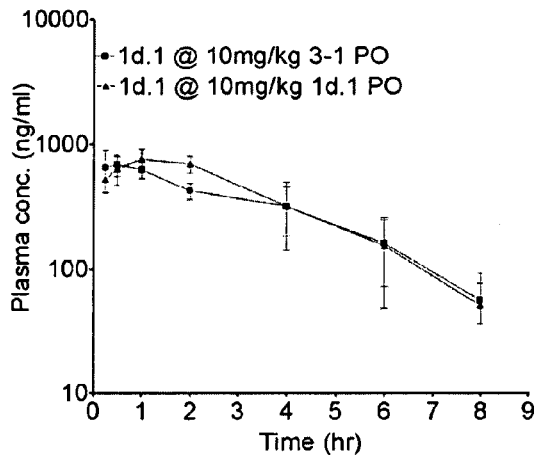
FIGS. 3a-3d comprise four graphs showing the pharmacokinetic properties of compounds 2-1 and 3-1 in dogs and rats and of 1d.1 in the rat.

FIG. 3a shows that the rat plasma concentration time profile of compound 1d.1 from 3-1 and 1d.1 administered orally are indistinguishable. No 3-1 was detected in rat plasma after oral administration of 3-1.

Figure 3B:
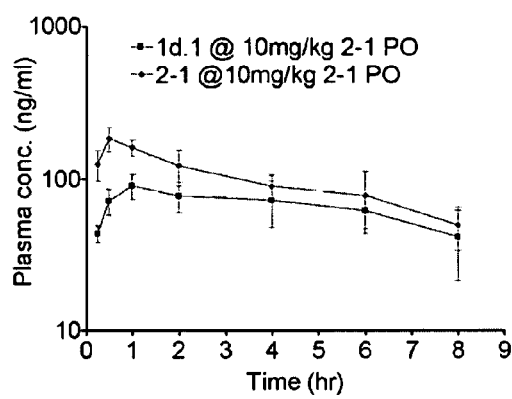

FIG. 3b shows the rat plasma concentration time profile of compound 1d.1 and 2-1 after oral administration of 2-1.

Figure 3C:
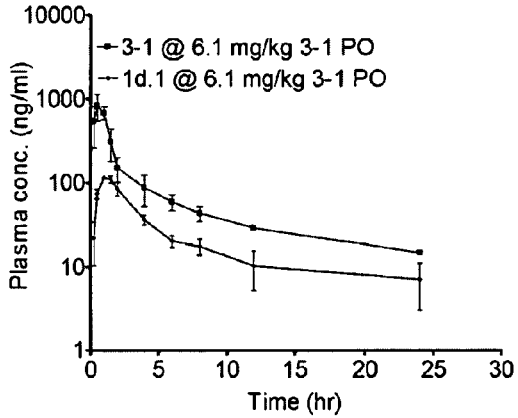

FIG. 3c shows the dog plasma concentration time profile of compound 1d.1 and 3-1 after oral administration of 3-1.

Figure 3D:
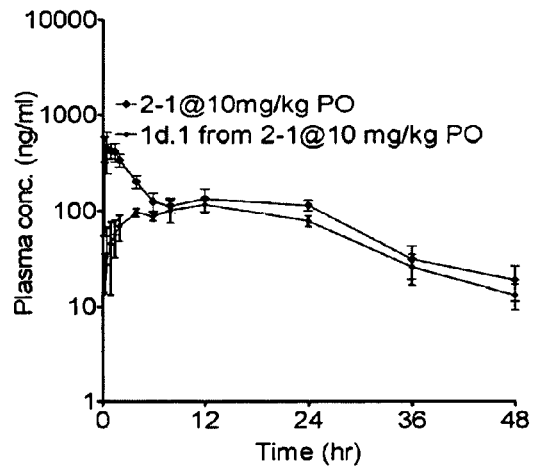

FIG. 3d shows the dog plasma concentration time profile of compound 1d.1 and 2-1 after oral administration of 2-1.

These figures show that the plasma half-life of 1d.1 upon oral administration of compound 2-1 is 2-3 times greater than upon oral administration of compound 3-1.

EXAMPLE 7

Vesicular Monoamine Transporter Isoform 2 (VMAT2) Binding Assay (Adapted from Teng, et al., J. Neurochem. 71, 258-65, 1998)

Procedure A:
Preparation of Rat Striatal Vesicles

Rat striata from three rats are pooled and homogenized in 0.32 M sucrose. The homogenate is then centrifuged at 2,000×g for 10 min at 4° C. and the resulting supernatant is centrifuged at 10,000×g for 30 min at 4° C. The resulting pellet containing the enriched synaptosomal fraction (2 mL) is subjected to osmotic shock by addition of 7 mL of distilled $H_2O$, and subsequently the suspension is homogenized. The osmolarity is restored by the addition of 0.9 mL of 0.25 M HEPES and 0.9 mL of 1.0 M neutral L-(+)-tartaric acid dipotassium salt buffer (pH 7.5), followed by a 20 min centrifugation (20,000×g at 4° C.). The supernatant is then centrifuged for 60 min (55,000×g at 4° C.) and the resulting supernatant is centrifuged for 45 min (100,000×g at 4° C.). The resulting pellet is resuspended in 25 mM HEPES, 100 mM L-(+)-tartaric acid dipotassium salt, 5 mM $MgCl_2$, 10 mM NaCl, 0.05 mM EGTA, pH 7.5 to a protein concentration of 1-2 mg/mL and stored at −80° C. for up to 3 weeks without appreciable loss of binding activity. Immediately before use, the final pellet is resuspended in binding buffer (25 mM HEPES, 100 mM L-(+)-tartaric acid dipotassium salt, 5 mM MgCl2, 10 mM NaCl, 0.05 mM EGTA, 0.1 mM EDTA, 1.7 mM ascorbic acid, pH 7.4). [$^3$H]-dihydrotetrabenazine (DHTBZ) Binding Aliquots of the vesicle suspension (0.16 mL, 15 µg of protein/mL) are incubated with competitor compounds (ranging from 1E-6M to 1E-12M) and 2 nM [$^3$H]-dihydrotetrabenazine (HTBZ; specific activity: 20 Ci/mmol, American Radiolabeled Chemicals, Inc) for 1 h at room temperature in a total volume of 0.5 mL. The reaction is terminated by rapid filtration of the samples onto Whatman GF/F filters using a Brandel cell harvester. Nonspecific binding is determined using 20 µM tetrabenazine (TBZ). Filters are previously soaked for 2 h with ice-cold polyethyleneimine (0.5%). After the filters are washed three times with the ice-cold buffer, they are placed into scintillation vials with 10 mL scintillation cocktail. Bound radioactivity is determined by scintillation spectrometry.

Procedure B:

The procedure was adapted from that described previously (Near, (1986), Mol. Pharmacol. 30: 252-7). Homogenates from Sprague-Dawley rat forebrain were prepared by homogenization and washing by centrifugation as described previously (Hoare et al., (2003) Peptides 24:1881-97). In a total volume of 0.2 mL in low-binding 96-well plates (Corning #3605), twelve concentrations of HTBZ isomer or analog were competed against 6 nM $^3$H-dihydrotetrabenezine (American Radiolabeled Chemicals, Kd 2.6 nM) on rat forebrain homegenate (100 μg membrane protein per well), in VMAT2 binding buffer (Dulbecco's phosphate buffered saline, 1 mM EDTA, pH 7.4). Following incubation at 25° C. for two hours, bound radioligand was collected by rapid filtration onto GF/B glass fiber filters using a Unifilter-96 Harvester (PerkinElmer). Filter plates were pre-treated for 10 minutes with 0.1% polyethylenimine and following harvesting washed with 800 μl VMAT2 binding buffer. Bound radioligand was quantified by scintillation counting using a Topcount NXT (PerkinElmer).

TABLE 1

VMAT2 affinity from competition binding studies

| Compound | pKi (n) | Ki (nM) |
| --- | --- | --- |
| 2R, 3R, 11bR-HTBZ | 8.7 ± 0.2 (6) | 1.9 |
| 2S, 3R, 11bR-HTBZ | 7.9 ± 0.1 (5) | 13 |
| 2S, 3S, 11bS-HTBZ | 6.7 ± 0.1 (3) | 202 |
| 2R, 3S, 11bS-HTBZ | 6.1 ± 0.1 (4) | 714 |
| Compound 3-1 | 7.9 ± 0.1 (2) | 14 |
| Compound 2-1 | 6.7 ± 0.2 (2) | 187 |

Data are mean ±SD for at least two independent experiments. Ki values were determined using a published Kd value of 1.2 nM for rat striatal membranes (Roland et al., 2000).

EXAMPLE 8

Receptor Selectivity Binding Assays

The four HTBZ stereoisomers and compounds of the present invention were tested for receptor specificity by screening against a panel of 80 receptors, ion channels and transporters (High-throughput profile, Cerep, S.A.). Subsequently, the compounds were tested in selected competition binding assays over a range of concentrations to determine their affinity for the receptors described below.

(a) Dopamine D2S receptor:
Reference: Grandy et al., (1989) Proc. Natl. Acad. Sci. USA 86: 9762-6
Source: Human recombinant (CHO cells)
Ligand: [3H]spiperone, 1.0 nM
Incubation time/temperature: 90 min/25° C.
Incubation buffer: 50 mM HEPES, 100 mM NaCl, 1 mM EDTA, 3 mM MgCl$_2$, pH 7.4
Non-specific ligand: clozapine (10 μM)
Kd: 27 pM
Bmax: 6.9 pmol/mg
Specific binding: 600 cpm
Quantitation method: Scintillation counting (b) Dopamine D4.4 receptor:
Reference: Van Tol et al. (1992) Nature, 358: 149-152.
Source: Human recombinant (CHO cells)
Ligand: [3H]spiperone, 0.3 nM
Incubation time/temperature: 60 min./22° C.
Non-specific ligand: (+)butaclamol (10 μM)
Kd: 0.19 nM
Quantitation method: Scintillation counting

TABLE 2

Receptor selectivity binding data

| | 2R, 3R, 11bR-HTBZ | 2S, 3R, 11bR-HTBZ | 2S, 3S, 11bS-HTBZ | 2R, 3S, 11bS-HTBZ | 3-1 | 2-1 |
| --- | --- | --- | --- | --- | --- | --- |
| D2S (h) | −6% inhibition at 10 uM | 17% inhibition at 30 uM | 192 | 57 | 15% inhibition at 10 uM | 2% inhibition at 10 uM |
| D4.4 (h) | 0% inhibition at 1 uM | 30% inhibition at 10 uM | 9% inhibition at 1 uM | 67 | 15% inhibition at 10 uM | 13% inhibition at 10 uM |

Values shown are either Ki (nM) or % inhibition at the concentration tested.

2R, 3R, 11bR-HTBZ and the two structural analogs of 2R, 3R, 11bR-HTBZ, compounds 2-1 and 3-1, demonstrated selectivity for VMAT2. In contrast, the 2S, 3S, 11bS and 2R, 3S, 11bS HTBZ stereoisomers exhibited high affinity binding to D2(S). The 2S, 3R, 11bR HTBZ showed some minor inhibition at the dopamine receptors tested. This off-target activity of certain HTBZ isomers might contribute to some of the side effects observed with TBZ.

EXAMPLE 9

VMAT2 Inhibitor-Induced Reductions in Locomotor Activity

Rats (Sprague-Dawley, 100-300 g) are adapted to single housing for at least 3 days prior to testing. Rats are administered test substances by oral, intraperitoneal, subcutaneous or intravenous routes (between 1-100 mg/kg) or vehicle controls. Following a pre-treatment time of 15-60 minutes, rats are placed in a clear cage surrounded by photocell detectors (San Diego Instruments). Rat locomotor activity is detected by breaks in the photocell beams and activity is defined as the number of beam breaks per session. Observation periods range from 15 min to 2 hours. Novel compound effects are compared with the effects of vehicle and positive control (diazepam at 3 mg/kg) with one-way ANOVA, followed by Student's Neuman-Keul's post hoc analyses. 8-10 rats are used per test condition.

EXAMPLE 10

VMAT2 Inhibitor-Induced Ptosis

Rats (Sprague-Dawley, 100-300 g) are adapted to single housing for at least 3 days prior to testing. Rats are administered test substances by oral, intraperitoneal, subcutaneous or intravenous routes (between 1-100 mg/kg) or vehicle controls. Following a pre-treatment time of 15 minutes, rats are placed in a clear cage for observation of ptosis. Ptosis is evaluated on a 4 point scale: Eyes fully open=0, eyes ¼ closed=1, eyes ½ closed=2, eyes ¾ closed=4, eyes fully closed=4. Measurements are taken at 15 minute intervals up to 3 hours after administration of compounds. Novel compound effects are compared with the effects of vehicle with one-way ANOVA, followed by Student's Neuman-Keul's post hoc analyses. 8-10 rats are used per test condition.

It will be appreciated that, although specific embodiments of the invention have been described herein for purposes of illustration, various modifications may be made without departing from the spirit and scope of the invention. Accordingly, the invention is not limited except as by the appended claims.

I claim:

1. (S)-2-Amino-3-methyl-butyric acid (2R,3R, 11bR)-3-isobutyl-9,10-dimethoxy-1,3,4,6,7,11b-hexahydro-2H-pyrido [2,1-a]isoquinolin-2-yl ester or a pharmaceutically acceptable salt thereof.

2. A pharmaceutical composition comprising a compound according to claim 1 and a pharmaceutically acceptable carrier or diluent.

* * * * *

UNITED STATES PATENT AND TRADEMARK OFFICE
CERTIFICATE OF CORRECTION

PATENT NO. : 8,039,627 B2
APPLICATION NO. : 11/937445
DATED : October 18, 2011
INVENTOR(S) : Kyle W. Gano Page 1 of 1

It is certified that error appears in the above-identified patent and that said Letters Patent is hereby corrected as shown below:

ON THE TITLE PAGE

Item (56):
"WO W091/16920 A1 11/1991" should read, --WO WO91/16920 A1 11/1991--.

Item (56):
"WO W02007/017643 A1 2/2007" should read, --WO WO2007/017643 A1 2/2007--.

Item (56) under Other Publications on page 2, column 1, line 1,
"Lorenz!, P.L. et al, Amino Acid Ester Prodrugs of 2-Bromo-5,6-dichloro-1-(beta-D-ribofuranosyl)benzimidazole Enhance Metabolic Stability in Vitro and in Vivo, The Journal of Pharmacology and Experimental Therapeutics, 2005, 883-890, 314(2)." should read,
--Lorenzi, P.L. et al, Amino Acid Ester Prodrugs of 2-Bromo-5,6-dichloro-1-(beta-D-ribofuranosyl)benzimidazole Enhance Metabolic Stability in Vitro and in Vivo, The Journal of Pharmacology and Experimental Therapeutics, 2005, 883-890, 314(2).--.

Signed and Sealed this
Thirteenth Day of March, 2012

David J. Kappos
*Director of the United States Patent and Trademark Office*

UNITED STATES PATENT AND TRADEMARK OFFICE
CERTIFICATE OF CORRECTION

PATENT NO. : 8,039,627 B2
APPLICATION NO. : 11/937445
DATED : October 18, 2011
INVENTOR(S) : Gano et al.

It is certified that error appears in the above-identified patent and that said Letters Patent is hereby corrected as shown below:

On the Title Page

Item (12), should read:
Gano et al.

Item (75), should read:
Kyle W. Gano, San Diego, CA (US);
Nicole Harriott, San Diego, CA (US)

Signed and Sealed this
Eighteenth Day of January, 2022

Drew Hirshfeld
*Performing the Functions and Duties of the*
*Under Secretary of Commerce for Intellectual Property and*
*Director of the United States Patent and Trademark Office*